(12) United States Patent
Brown et al.

(10) Patent No.: US 6,410,230 B1
(45) Date of Patent: *Jun. 25, 2002

(54) GLYCERALDEHYDE-3-PHOSPHATE DEHYDROGENASE AND NUCLEAR RESTORATION OF CYTOPLASMIC MALE STERILITY

(75) Inventors: Gregory G. Brown, Montreal; Benoit Landry, L'Acadie; Martine Jean, Sainte-Foy, all of (CA)

(73) Assignee: McGill University, Montreal (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/219,194

(22) Filed: Dec. 23, 1998

Related U.S. Application Data

(63) Continuation of application No. PCT/CA97/00424, filed on Jun. 16, 1997.
(60) Provisional application No. 60/020,533, filed on Jun. 26, 1996.

(51) Int. Cl.$^7$ .............................. C12Q 1/68; C12P 19/34
(52) U.S. Cl. ............................ 435/6; 435/91.2; 536/24.3
(58) Field of Search ..................... 435/6, 91.2; 536/24.3

(56) References Cited

PUBLICATIONS

Singh M. et al.: "*Gentics*", vol. 143. No. 1, May 1996; pp. 505–515.
Wise R. et al. "*Theoretical and Applied Gentics*", vol. 88, No. 6–7, 1994; pp. 785–795.
Delourme R. et al. "*Theoretical and Applied Genetics*", vol. 88, No. 6–7, 1994;pp. 741–748.
Schnable P. et al; "*Genetics*", vol. 136, No. 3, 1994. pp. 1171–1185.

*Primary Examiner*—Jeffrey Fredman
*Assistant Examiner*—Juliet C. Einsmann
(74) *Attorney, Agent, or Firm*—Nixon Peabody LLP

(57) ABSTRACT

The instant invention provides a method for detecting the presence of a restorer gene in the nuclear genomic DNA of a Brassica plant comprising the use of a probe/primer comprising the sequence of the Brassica glyceraldehyde-3-phosphate dehydrogenase (SEQ ID NO: 1) or a sufficient hybridizing fragment thereof.

2 Claims, 8 Drawing Sheets

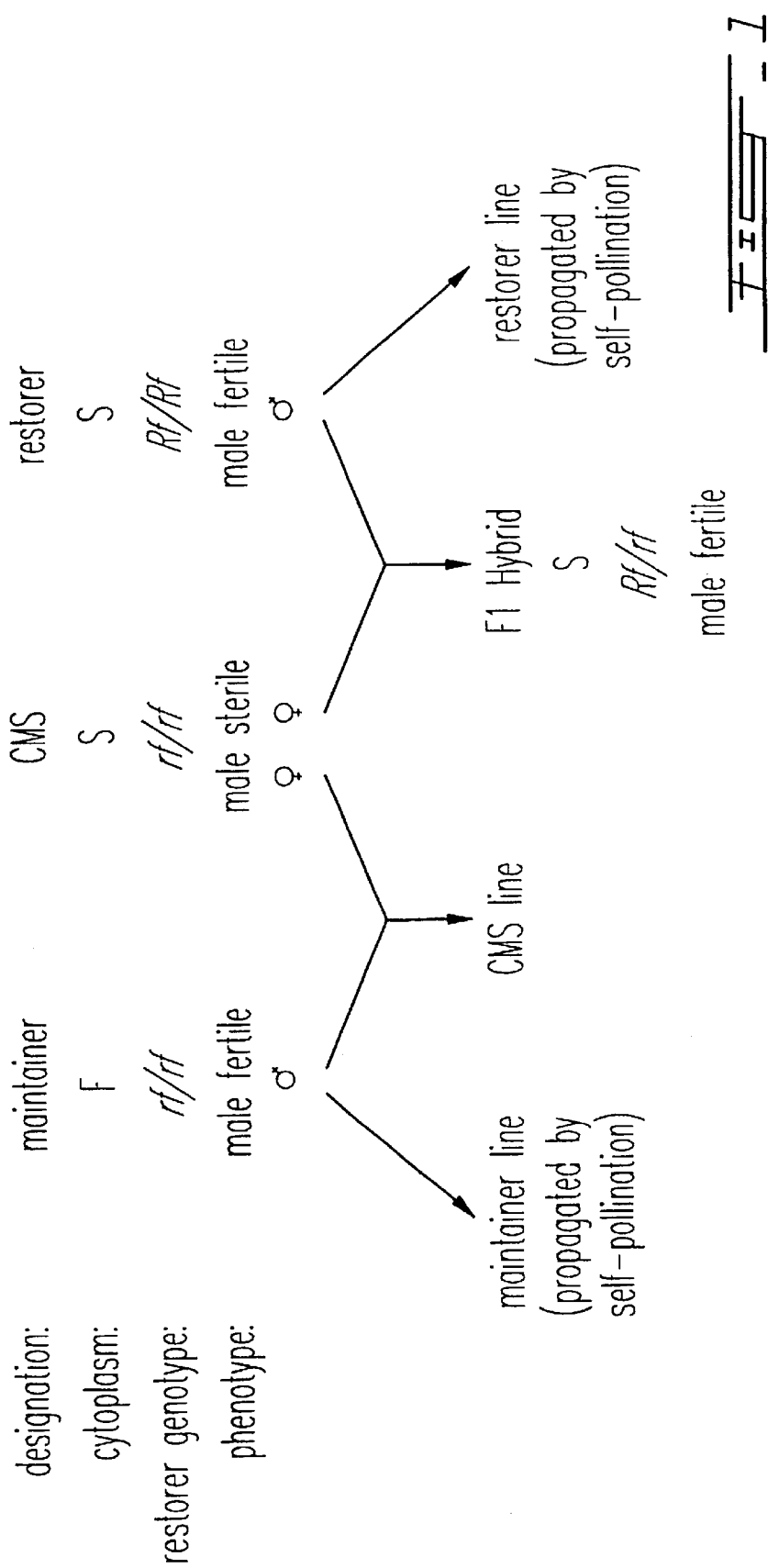

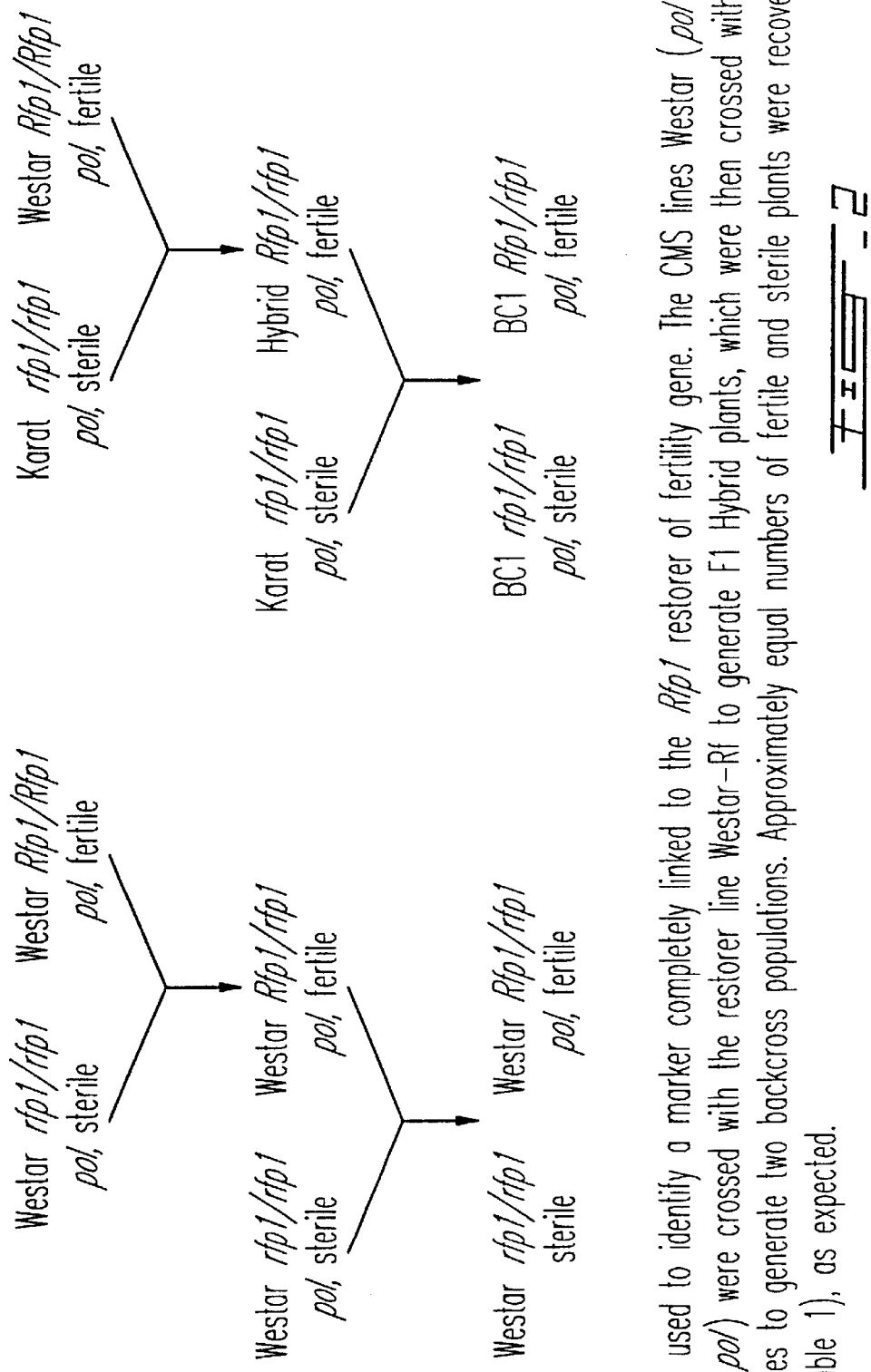

Crosses used to identify a marker completely linked to the *Rfp1* restorer of fertility gene. The CMS lines Westar (*pol*) and Karat (*pol*) were crossed with the restorer line Westar-Rf to generate F1 Hybrid plants, which were then crossed with the two CMS lines to generate two backcross populations. Approximately equal numbers of fertile and sterile plants were recovered (see Table 1), as expected.

FIG. 2

Comparison of Brassica napus cDNA clone 2NC10 with cytoplasmic glyceraldehyde-3-phosphate dehydrogenase (GAPC) cDNAs from Sinapis alba and Arabidopsis thaliana.

```
Brassica napus clone 2NC10      tctcgatctc atcgacaccc tct-------  -------gatatc
Sinapis alba GAPC               ---------- ---------- ---------   -------tttc
Arabidopsis thaliana GAPC       ---------- ----ctc atcttcaacc tctctctaac tctcgttttc 41  ga------aa tggctgacaa gaagattaag atcggaatca acggtttcgg aagaatcggt
     ga------aa tggctgacaa gaagattaag atcggaatca acggtttcgg aagaatcggt
     gattctacaa tggctgacaa gaagattagg atcggaatca acggattcgg aagaattggt 101  cgcttggtgg ctagagttat ccttcagagg aacgatgttg agctcgtcgc tgttaacgac
     cgtttggtgg ctagagttat ccttcagagg aacgatgttg agctcgtcgc tgttaacgat
     cgtttggttg ctagagttgt tctccagagg gacgatgttg agctcgtcgc tgtcaacgac 161  cccttcatca ccaccgagta catgacgtac atgtttaagt atgacagtgt tcacggtcag
     cccttcatca ccaccgagta catgacgtac atgtttaagt atgacagtgt tcatggtcag
     cccttcatca ctactgagta catgacctac atgttcaagt atgacagtgt acgacggtcaa
```

FIG. 3A

```
221  tggaagcaca  acgagctcaa  ggttaaggat  gagaagacac  ttctcttcgg  tgagaagcct
     tggaagcaca  atgagctcaa  ggtgaaggat  gagaaaacac  ttctcttcgg  agagaagcct
     tggaaacaca  atgaactcaa  gatcaaggat  gagaagaccc  ttctcttcgg  tgagaagcca 281  gtcactgttt  tcggcatcag  gaaccctgag  gatatgccca  tggggtgagg  ctggagctga
     gtcactgttt  tcggcatcag  gaaccctgag  gatat-ccca  tggggtgagg  ccggagctga
     gtcactgttt  tcggcatcag  gaaccctgag  gatat-ccca  tgggccgagg  ctggagctga 341  ctttggggtt  gagtctactg  gtgtcttcac  cgacaaggac  aaggctgctg  ctcacttgaa
     ctttgttgtt  gagtctactg  gtgtcttcac  tgacaaggac  aaggctgctg  ctcacttgaa
     ctacgttgtt  gagtctactg  gtgtcttcac  tgacaaagac  aaggctgcag  ctcacttgaa 401  gggtggtgcg  aagaaagttg  tcatctctgc  accaagcaaa  gatgctccca  tgttcgttgt
     gggtggtgcc  aagaaagttg  tcatctctgc  accaagcaaa  gatgctccta  tgttcgttgt
     gggtggtgcc  aagaaggttg  ttatctctga  acccagcaaa  gacgctccaa  tgtttgttgt 461  tggtgtcaat  gagcatgagt  acaagtctga  tctcaacatt  gtttccaacg  ctagt-gcac
     tggtgtcaat  gagcatgagt  acaagtctga  tctcaacatt  gtttccaacg  ctagttgcac
     tggtgtcaac  gagcacgaat  acaagtccga  ccttgacatt  gtctccaacg  ctagctgcac
```

FIG-3B 621  cactaactgc cttgctccac ttgccaaggt tatcancgac aggtttggaa ttgtcgaggg
     cactaactgc cttgctccac ttgccaaggt tatcaacgac aggtttggaa ttgtcgaggg
     cactaactgc cttgctcccc ttgccaaggt tatcaatgac agatttggaa ttgttgaggg 681  actcatgacc accgtccact ctatcactgc aactcagaag acagttgatg gtccatcaat
     actcatgact actgtccact ctatcactgc tactcagaag acagttgatg gtccatcaat
     tcttatgact acagtccact caatcactgc tactcagaag actgttgatg ggccttcaat 741  gaaggactgg agaggtggaa gagccgcttc cttcaacatc attcccagca gcaccggagc
     gaaggactgg agaggtggaa gagccgcttc cttcaacatc attcccagca gcaccggagc
     gaaggactgg agaggtggaa gagctgcttc attcaacatt attcccagca gcactggagc 801  tgccaaggct gtcggaaaagg ttcttccaca gctc--aacg gaaagctgac cggtatgtcc
     tgccaaggct gtcggaaagg tgcttccaca gctc--aatg gaaaattgac cggaatgtcc
     tgccaaggct gtcggaaagg tgcttcca--  gctcttaacg gaaagttgac tggaatgtct 861  ttccgtgttc ccaccgttga tgtttcagtt gttga-ctca cggttagact cgagaaagct
     ttccgtgttc ccaccgttga tgtttcagtt gtcgacctca cggttagact cgagaaagct
     ttccgtgtcc caaccgttga tgtctcagtt gttgacctta ctgtcagact cgagaaagct

*Fig. 3C*

```
 921  gcaacctacg atgaaatcaa gaaggctatc aaggaggaat ctgagggcaa gctaaaggga
      gcaacctacg atgaaatcaa gaaggctatc aaggaggagt ctcagggcaa gctaaaggga
      gctacctacg aagaaatcaa aaaggctatc aaggaggaat ccgaaggcaa actcaaggga 981  atccttggtt acacagagga tgatgttgtc tcaaccgact tcgttggtga caacaggtcg
      atccttggtt acacagagga tgatgttgtc tcaactgact tcgttggtga caacaggtcg
      atccttggat acaccgagga tgatgttgtc tcaactgact tcgttggcga caacaggtcg 1041  agcattttg  acgcaaaggc tggaatcgcg ttgagtgaca actttgtgaa gctggtgtcg
      agcatctttg acgccaaggc tggaatcgca ttgagtgaca acttcgtgaa gctggtgtcg
      agcattttg  acgccaaggc tggaattgca ttgagcgaca agtttgtgaa attggtgtca 1101  tggtacgaca acgaatgggg ttacagtacc cgtgtggtcg acttgatcat tcacatgtcc
      tggtatgaca acgaatgggg ttacagtacc cgtgtggtcg acttgatcat tcatatgtcc
      tggtacgaca acgaatgggg ttacagttcc cgtgtggtcg acttgatcgt ccacatgtca 1161  aaggcctaag tcgatga---  --agatctcg agtgat--gt aatgg----- ----------
      aaggcctaaa acgctga---  --agatctac aatgat--gt aatgg----- ----------
      aaggcctaa- ---gctaagaa gcagatctcg aatgataggg agtgaaagt  catctgttca
```

FIG. 3D

```
1221 --------- tgttttaaa ttgttgtttt tatcgaataa atttct-tg ggttttgaaa
     --------- tg-tcttaat ttgtggtttt ---cgaataa gatttctttg gg--------
     tccccttta tggtctgaat ttgtcgtttt ---cgaataa aatttctttg aacttggaa- 1281 cctttatgg- -ttttgg--- ---cgaattct ctactttcac gtgacgtgat aagaagtttg
     --------- --------- --------- --------- --------- ---------
     -cttttttt ttttggttt tcttaattct ca---ttcat gtgaggtgat -gggagtttg 1341 tagaccggtt gttttttatt tttactga-- --------- --------- ---------
     --------- --------- --------- --------- --------- ---------
     tagaccg-at g------- t tttactggaa gcccttgtt tttggctttt gatatattga 1401 --------- --------- --------- --------- ---
     --------- --------- --------- --------- ---
     gttaacgtta tggttttaaa aaaaaa
```

FIG. 3E

Polymorphism detected by cRF1 probe in *Brassica napus* and a genetic population segregating for the *Rfp1* gene. Fertile plants have the *Rfp1* gene, sterile plants do not. Arrow indicates the polymorphic restriction fragment associated with fertility restoration.

Rf=Restorer line parent
F=fertile plant
S=sterile plant

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 1207 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

| | | | | | |
|---|---|---|---|---|---|
| TCTCGATCTC | ATCGACACCC | TCTGATATCG | AAATGGCTGA | CAAGAAGATT A AGATCGGAA | 60 |
| TCAACGGTTT | CGGAAGAATC | GGTCGCTTGG | TGGCTAGAGT | TATCCTTCAG A GGAACGATG | 120 |
| TTGAGCTCGT | CGCTGTTAAC | GACCCCTTCA | TCACCACCGA | GTACATGACG T ACATGTTTA | 180 |
| AGTATGACAG | TGTTCACGGT | CAGTGGAAGC | ACAACGAGCT | CAAGGTTAAG G ATGAGAAGA | 240 |
| CACTTCTCTT | CGGTGAGAAG | CCTGTCACTG | TTTTCGGCAT | CAGGAACCCT G AGGATATGC | 300 |
| CCATGGGGTG | AGGCTGGAGC | TGACTTTGGG | GTTGAGTCTA | CTGGTGTCTT C ACCGACAAG | 360 |
| GACAAGGCTG | CTGCTCACTT | GAAGGGTGGT | GCGAAGAAAG | TTGTCATCTC T GCACCAAGC | 420 |
| AAAGATGCTC | CCATGTTCGT | TGTTGGTGTC | AATGAGCATG | AGTACAAGTC T GATCTCAAC | 480 |
| ATTGTTTCCA | ACGCTAGTGC | ACCACTAACT | GCCTTGCTCC | ACTTGCCAAG G TTATCANCG | 540 |
| ACAGGTTTGG | AATTGTCGAG | GGACTCATGA | CCACCGTCCA | CTCTATCACT G CAACTCAGA | 600 |
| AGACAGTTGA | TGGTCCATCA | ATGAAGGACT | GGAGAGGTGG | AAGAGCCGCT T CCTTCAACA | 660 |
| TCATTCCCAG | CAGCACCGGA | GCTGCCAAGG | CTGTCGGAAA | GGTTCTTCCA C AGCTCAACG | 720 |
| GAAAGCTGAC | CGGTATGTCC | TTCCGTGTTC | CCACCGTTGA | TGTTTCAGTT G TTGACTCAC | 780 |
| GGTTAGACTC | GAGAAAGCTG | CAACCTACGA | TGAAATCAAG | AAGGCTATCA A GGAGGAATC | 840 |
| TGAGGGCAAG | CTAAAGGGAA | TCCTTGGTTA | CACAGAGGAT | GATGTTGTCT C AACCGACTT | 900 |
| CGTTGGTGAC | AACAGGTCGA | GCATTTTTGA | CGCAAAGGCT | GGAATCGCGT T GAGTGACAA | 960 |
| CTTTGTGAAG | CTGGTGTCGT | GGTACGACAA | CGAATGGGGT | TACAGTACCC G TGTGGTCGA | 1020 |
| CTTGATCATT | CACATGTCCA | AGGCCTAAGT | CGATGAAGAT | CTCGAGTGAT G TAATGGTGT | 1080 |
| TTTTAAATTG | TTGTTTTTAT | CGAATAAATT | TTCTTGGGTT | TTGAAACCTT T ATGGTTTTG | 1140 |
| GCGAATTCTC | TACTTTCACG | TGACGTGATA | AGAAGTTTGT | AGACCGGTTG T TTTTTATTT | 1200 |
| TTACTGA | | | | | 1207 |

(2) INFORMATION FOR SEQ ID NO: 2:

(i) SEQUENCE CHARACTERISTICS:
        (A) LENGTH: 1091 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

| | | | | | |
|---|---|---|---|---|---|
| TTTCGAAATG | GCTGACAAGA | AGATTAAGAT | CGGAATCAAC | GGTTTCGGAA G AATCGGTCG | 60 |
| TTTGGTGGCT | AGAGTTATCC | TTCAGAGGAA | CGATGTTGAG | CTCGTCGCTG T TAACGATCC | 120 |
| CTTCATCACC | ACCGAGTACA | TGACGTACAT | GTTTAAGTAT | GACAGTGTTC A TGGTCAGTG | 180 |
| GAAGCACAAT | GAGCTCAAGG | TGAAGGATGA | GAAAACACTT | CTCTTCGGAG A GAAGCCTGT | 240 |
| CACTGTTTTC | GGCATCAGGA | ACCCTGAGGA | TATCCCATGG | GGTGAGGCCG G AGCTGACTT | 300 |
| TGTTGTTGAG | TCTACTGGTG | TCTTCACTGA | CAAGGACAAG | GCTGCTGCTC A CTTGAAGGG | 360 |
| TGGTGCCAAG | AAAGTTGTCA | TCTCTGCACC | AAGCAAAGAT | GCTCCTATGT T CGTTGTTGG | 420 |
| TGTCAATGAG | CATGAGTACA | AGTCTGATCT | CAACATTGTT | CCAACGCTA G TTGCACCAC | 480 |
| TAACTGCCTT | GCTCCACTTG | CCAAGGTTAT | CAACGACAGG | TTTGGAATTG T CGAGGGACT | 540 |
| CATGACTACT | GTCCACTCTA | TCACTGCTAC | TCAGAAGACA | GTTGATGGTC C ATCAATGAA | 600 |

-continued

```
GGACTGGAGA GGTGGAAGAG CCGCTTCCTT CAACATCATT CCCAGCAGCA C CGGAGCTGC        660

CAAGGCTGTC GGAAAGGTGC TTCCACAGCT CAATGGAAAA TTGACCGGAA T GTCCTTCCG        720

TGTTCCCACC GTTGATGTTT CAGTTGTCGA CCTCACGGTT AGACTCGAGA A AGCTGCAAC        780

CTACGATGAA ATCAAGAAGG CTATCAAGGA GGAGTCTCAG GGCAAGCTAA A GGGAATCCT        840

TGGTTACACA GAGGATGATG TTGTCTCAAC TGACTTCGTT GGTGACAACA G GTCGAGCAT        900

CTTTGACGCC AAGGCTGGAA TCGCATTGAG TGACAACTTC GTGAAGCTGG T GTCGTGGTA        960

TGACAACGAA TGGGGTTACA GTACCCGTGT GGTCGACTTG ATCATTCATA T GTCCAAGGC       1020

CTAAAACGCT GAAGATCTAC AATGATGTAA TGGTGTCTTA ATTTGTGGTT T TCGAATAAG       1080

ATTTCTTTGG G                                                             1091
```

(2) INFORMATION FOR SEQ ID NO: 3:

(i) SEQUENCE CHARACTERISTICS:
        (A) LENGTH: 1295 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

```
CTCATCTTCA ACCTCTCTCT AACTCTCGTT TTCGATTCTA CAATGGCTGA C AAGAAGATT         60

AGGATCGGAA TCAACGGATT CGGAAGAATT GGTCGTTTGG TTGCTAGAGT T GTTCTCCAG        120

AGGGACGATG TTGAGCTCGT CGCTGTCAAC GACCCCTTCA TCACTACTGA G TACATGACC        180

TACATGTTCA AGTACGACAG TGTTCACGGT CAATGGAAAC ACAATGAACT C AAGATCAAG        240

GATGAGAAGA CCCTTCTCTT CGGTGAGAAG CCAGTCACTG TTTTCGGCAT C AGGAACCCT        300

GAGGATATCC CATGGGCCGA GGCTGGAGCT GACTACGTTG TTGAGTCTAC T GGTGTCTTC        360

ACTGACAAAG ACAAGGCTGC AGCTCACTTG AAGGGTGGTG CCAAGAAGGT T GTTATCTCT        420

GAACCCAGCA AAGACGCTCC AATGTTTGTT GTTGGTGTCA ACGAGCACGA A TACAAGTCC        480

GACCTTGACA TTGTCTCCAA CGCTAGCTGC ACCACTAACT GCCTTGCTCC C CTTGCCAAG        540

GTTATCAATG ACAGATTTGG AATTGTTGAG GGTCTTATGA CTACAGTCCA C TCAATCACT        600

GCTACTCAGA AGACTGTTGA TGGGCCTTCA ATGAAGGACT GGAGAGGTGG A AGAGCTGCT        660

TCATTCAACA TTATTCCCAG CAGCACTGGA GCTGCCAAGG CTGTCGGAAA G GTGCTTCCA        720

GCTCTTAACG GAAAGTTGAC TGGAATGTCT TTCCGTGTCC CAACCGTTGA T GTCTCAGTT        780

GTTGACCTTA CTGTCAGACT CGAGAAAGCT GCTACCTACG AAGAAATCAA A AAGGCTATC        840

AAGGAGGAAT CCGAAGGCAA ACTCAAGGGA ATCCTTGGAT ACACCGAGGA T GATGTTGTC        900

TCAACTGACT TCGTTGGCGA CAACAGGTCG AGCATTTTTG ACGCCAAGGC T GGAATTGCA        960

TTGAGCGACA AGTTTGTGAA ATTGGTGTCA TGGTACGACA ACGAATGGGG T TACAGTTCC       1020

CGTGTGGTCG ACTTGATCGT CCACATGTCA AAGGCCTAAG CTAAGAAGCA G ATCTCGAAT       1080

GATAGGGAGT GGAAAGTCAT CTGTTCATCC CCTTTTATGG TCTGAATTTG T CGTTTTCGA       1140

ATAAAATTTC TTTGAACTTG GAACTTTTTT TTTTTTGGT TTTCTTAATT C TCATTCATG       1200

TGAGGTGATG GGAGTTTGTA GACCGATGTT TTACTGGAAG CCCTTTGTTT T TGGCTTTTG       1260

ATATATTGAG TTAACGTTAT GGTTTTAAAA AAAAA                                   1295
```

GLYCERALDEHYDE-3-PHOSPHATE
DEHYDROGENASE AND NUCLEAR
RESTORATION OF CYTOPLASMIC MALE
STERILITY

CROSS-REFERENCE TO RELATED
APPLICATIONS

This application is a continuation of PCT/CA97/00424 filed Jun. 16, 1997 which claimed benefit under 35 U.S.C. §119 of U.S. provisional application No. 60/020,533, filed Jun. 26, 1996.

BACKGROUND OF THE INVENTION (a) Field of the Invention

The invention relates to a marker for nuclear restoration of cytoplasmic male sterility, and more particularly to the use of glyceraldehyde-3-phosphate dehydrogenase complementary DNA as such a marker. The invention also relates to a gene for nuclear restoration of cytoplasmic male sterility, and more particularly to the use of a form of the gene encoding glyceraldehyde-3-phosphate dehydrogenase for this purpose. Finally, the invention relates to the production of restorer lines directly through genetic transformation of plants with such a gene.

(b) Description of Prior Art

Hybrids of different crop varieties may show yields that are considerably greater than those of the parental lines. This phenomenon is known as hybrid vigor. To implement the use of hybrid vigor it is necessary to have a method available for preventing self-pollination of one or both of the parent lines in the hybrid cross. Mechanical, chemical and genetic methods are available for accomplishing this. One established genetic method involves the trait of cytoplasmic male sterility (CMS). The genetic determinants for CMS, the maternally transmitted inability to produce viable pollen, reside on the mitochondrial genome. Because CMS plants are male sterile, all of the seed that forms on them will necessarily be hybrid. Due to the maternal transmission of CMS, however, such F1 hybrids will also normally be male-sterile and hence be unable to self-fertilize and produce seed. To address this problem, specific nuclear genes that suppress the male sterile phenotype, termed restorers of fertility (Rf), can be incorporated into the pollinating parent of the hybrid cross. Genotypes on which the male sterile cytoplasm confers sterility are termed maintainers whereas those carrying Rf genes are termed restorers; the genes for the maintenance and restoration of CMS can be considered as different alleles (rf and Rf, respectively) at the same locus.

Shortcomings of Present Solutions

To produce a diverse set of hybrids using CMS, adequate numbers of restorer lines, that contain Rf genes, as well as "maintainer" lines, that are sterilized by the CMS cytoplasm, must be available. The use of such lines in hybrid crop production is outlined in FIG. 1. The development of these lines through conventional genetics is a slow process that minimally requires several years of effort and currently poses a major bottleneck in the generation of CMS-based hybrids in a number of crops, including canola, Canada's major cash crop. For example, to create a new restorer line it is necessary to first generate a hybrid between an existing restorer strain, which donates the Rf gene, and a recipient strain; a series of backcrosses to the recipient strain are then performed to incorporate the Rf gene without altering the strain's other desirable characteristics, a process termed introgression. Even after many generations some donor DNA that is linked to the Rf gene on the donor DNA will remain, a phenomenon termed linkage drag; this donor DNA may carry deleterious traits and compromise the quality of the recipient strain (Jean, M. et al., 1993, Current Topics in Molecular Genetics, 1:195–201).

This process can be expedited through the general process of indirect selection: progeny plants are first screened for genetic markers linked to the restorer gene rather than the restorer gene itself. These markers are chosen such that they can be screened for at a very early stage in plant development. This circumvents the costly procedure of raising many progeny plants to maturity and can considerably accelerate the introgression process. Restriction fragment length polymorphisms (RFLPs) represent a type of DNA marker that is ideally suited for this purpose. RFLPs are differences (between two genotypes) in restriction fragment patterns detected by specific DNA probes. Probes that detect fragment pattern differences between restorer and maintainer lines and that co-segregate with the Rf gene can be used to indirectly select for the restorer gene in a plant breeding program. We have obtained several probes that are linked to Rfp1, a restorer of the Polima or pol CMS, one of the two forms of CMS in canola (B. napus) that is currently being used in hybrid seed production. None of these markers is completely linked to the gene. This introduces an element of uncertainty into their use for indirect selection-the presence of any one marker in a plant does not guarantee the presence of the restorer gene in that plant. It therefore is necessary to employ a number of the markers for indirect selection of plant containing the restorer gene.

It would be highly desirable to be provided with a marker that is perfectly associated with nuclear restoration of cytoplasmic male sterility.

This process can be further expedited through direct introduction of a cloned restorer gene. We believe that the probe we have identified, which show perfect linkage to Rfp1 is detecting the restorer gene itself.

SUMMARY OF THE INVENTION

One aim of the present invention is to provide a marker for nuclear restoration associated with cytoplasmic male sterility.

Another aim of the present invention is to provide the use of glyceraldehyde-3-phosphate dehydrogenase complementary DNA as such a restorer marker.

Another aim of the present invention is to be able to use this gene to produce restorer lines directly through genetic transformation.

In accordance with the present invention there is provided a probe specific for nuclear restoration of cytoplasmic male sterility of plants, which comprises a glyceraldehyde-3-phosphate dehydrogenase cDNA or genomic DNA sequence, a hybridizing fragment thereof or any DNA sequence derived therefrom for use as primers for amplification of glyceraldehyde-3-phosphate dehydrogenase, wherein said DNA sequence or hybridizing fragment thereof hybridizes to specific DNA fragments characteristic of plants possessing a nuclear restorer gene under stringent conditions.

In accordance with the present invention there is also provided a gene for nuclear restoration of cytoplasmic male sterility in plants which comprises a DNA sequence encoding glyceraldehyde-3-phosphate dehydrogenase and surrounding sequences.

The surrounding sequences may be located 3' and/or 5' relative to the glyceraldehyde-3-phosphate dehydrogenase sequence and may be of about 50 kb.

In accordance with the present invention there is also provided a method of production of restorer lines, which comprises genetically transforming plants with the nuclear restoration of cytoplasmic male sterility gene of the present invention.

In accordance with the present invention, any plant species may be used provided that the restorer gene in the plant species corresponds to a specific form of GAPC. Such species include, without limitation, Brassica napus, other Brassica species, maize (Zea mays), rice (Oryza sativum), sunflower (Helianthus annuum) and sorghum (Sorghum bicolor).

BRIEF DESCRIPTION OF THE DRAWINGS

FIG. 1 is a schematic representation of the use of cytoplasmic male sterility (CMS) in hybrid seed production;

FIG. 2 shows the crosses used to identify a marker completely linked to the Rfp1 restorer of fertility gene;

FIGS. 3A to 3E show the comparison of Brassica napus cDNA clone cRF1 (SEQ ID NO:1) with cytoplasmic glyceraldehyde-3-phosphate dehydrogenase (GAPC) cDNAs from Sinapis alba (SEQ ID NO:2) and Arabidopsis thaliana (SEQ ID NO:3)

DETAILED DESCRIPTION OF THE INVENTION

Figure 4:
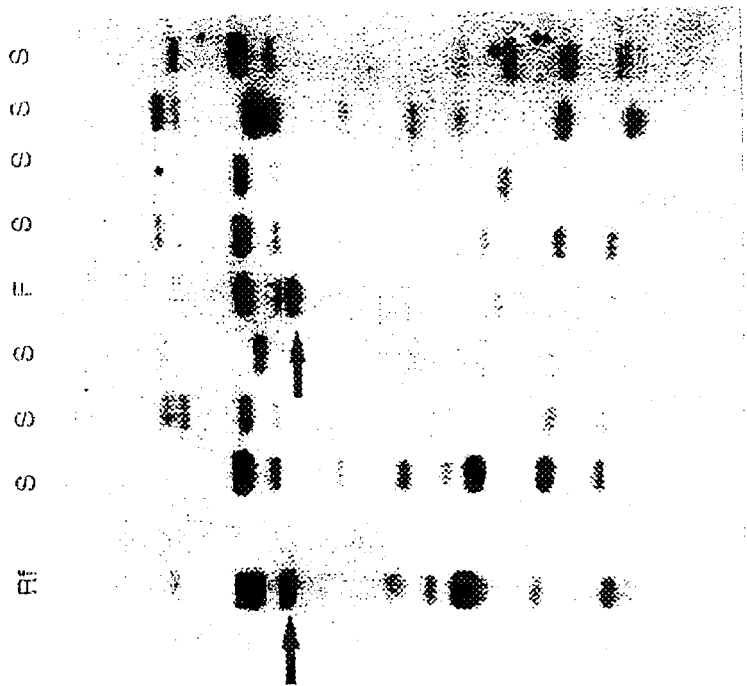
FIG. 4 illustrates a gel of the polymorphism detected by cRF1 probe in Brassica napus in a genetic population segregating for the Rfp1 gene.

We continued an analysis of two genetic crosses which gave rise to plant populations in which the restorer gene was segregating (outlined in FIG. 2). In each case, the nature of the cross was such that for linked markers, most sterile progeny individuals would show the RFLP characteristic of the male sterile parent of the cross, while most male fertile progeny plants would show the RFLP characteristic of the fertile parent. A new marker, designated cRF1, was found that is perfectly linked to this gene. Specifically, of the 175 individuals tested in the two crosses, all fertile progeny were found to possess the allele (or form) of the fertile parent while all sterile plants were found to possess the allele of the sterile parent (Table 1). cRF1 therefore represents a particularly powerful tool for indirect selection of the restorer gene.

TABLE 1

Co-segregation of an Rfp1-specific RFLP allele detected by the probe cRF1 (GAPC) with male fertility restoration in 2 Brassica napus backcross populations

| Cross | Fertile progeny plants | | Sterile progeny plants | |
|---|---|---|---|---|
| | with Rfp1-specific cRF1 allele | without Rfp1-specific cRF1 allele | with Rfp1-specific cRF1 allele | without Rfp1-specific cRF1 allele |
| Westar x Westar-Rf | 30 | 0 | 0 | 34 |
| Karat x Westar-Rf | 56 | 0 | 0 | 55 |
| Total | 86 | 0 | 0 | 89 |

Points of Difference with Previous Solutions

Because of the perfect linkage between cRF1 and Rfp1, the uncertainty in the use of this probe for indirect selection of the restorer gene is virtually eliminated.

In addition, no restorer gene for the Polima or pol CMS system has been isolated and hence production of restorer lines directly through genetic transformation is not possible. This should result in a significant reduction of the cost of the use of indirect selection in the development of new restorer (FIG. 4) lines.

The DNA probe that detected this polymorphism is a B. napus complementary DNA (cDNA), i.e., a DNA complementary to a messenger RNA molecule (mRNA). The DNA sequence of this cDNA was determined. Analysis of a nucleotide sequence database indicated that the cDNA's sequence is 99% similar to that of a cytoplasmic form of a glycolytic enzyme from Arabidopsis thaliana, glyceraldehyde-3-phosphate dehydrogenase (FIGS. 3A and 3B), which is encoded by the GAPC gene (Shih, M.-C. et al., 1991, Gene, 104:133–138). The perfect linkage between the restorer gene and the GAPC polymorphism leads us to believe that the restorer gene is likely to be specific form of GAPC.

We have conducted a similar type of analysis on a BC1 population in which the restorer gene for a different B. napus CMS, the nap, system was segregating and found that the nap restorer was simply a different allele of the same genetic locus Thus different forms of GAPC correspond to two different nuclear fertility restorer genes in B. napus. This result further suggests that other restorer genes may correspond to GAPC isoforms and that the relationship between GAPC and restorer genes may extend to other CMS systems in other plant species. No relationship between GAPC and restorer genes for any plant species has been suggested previously.

With this gene it may therefore be possible to construct restorer lines in a single step by using genetic transformation to introduce the restorer-specific GAPC gene into maintainer genotypes (genotypes that do not naturally contain the restorer). This would be extremely cost effective as it would eliminate many steps in the plant breeding process necessary for the development of such lines. If the association between GAPC and restorer genes is extended to other crop species, this would represent a general method for the isolation of restorer genes and the development of restorer lines in many crops.

The present invention will be more readily understood by referring to the following examples which are given to illustrate the invention rather than to limit its scope.

EXAMPLE I

Use of a GAPC Probe as an Indirect Selection Marker in the Production of a New Restorer Cell Line Three plant genotypes will be considered:

A a CMS line;

B a male fertile line that lacks the restorer gene and contains a male fertile cytoplasm; and R a male fertile line that contains the restorer gene and a male sterile cytoplasm.

It will be assumed that hybrids between lines A and B that are produced by manual genetic crosses show considerable hybrid vigour; hybrids between A and R do not. As line B lacks a restorer gene, it is not possible to produce male fertile hybrids of these two lines using CMS. If, however, the restorer gene could be transferred from line R to line B without otherwise altering the characteristics of line B, it would be possible to obtain male fertile hybrids between lines A and B using CMS. Traditionally, this would be done through a process termed introgression. Line R is crossed as a female with line B to produce a male fertile F1 hybrid of A and B that contains the male sterile cytoplasm (the cytoplasm of a hybrid is derived exclusively from the female parent) but is also male fertile because it has received a single copy of the restorer gene from the line R parent. A second cross (termed a backcross) is then performed between the hybrid (as female) and the line B. Large numbers of progeny grown are in the field, and equal numbers of steriles and fertiles are expected, fertiles possessing the restorer gene. One or more fertiles are then used as females in a second backcross to line B; fertile plants are recovered and crossed as females to line B for a third time. This process is repeated for many generations; with each new generation the progeny are expected to become more similar to line B (except they will possess the restorer gene). At each generation various characteristics associated with line B will be assessed. Eventually, new restorer line, with all or most of the desirable characteristics of line B will be produced. This line could then be used for the large scale production of hybrids between lines A and B.

The GAPC probe facilitates this process because it allows for the assessment of the presence of the restorer gene in progeny plants at the seedling stage. DNA is extracted from a small amount of leaf material, digested with a restriction endonuclease, such as HindIII (used in FIG. 4) and analyzed using the GAPC probe. The presence of the restriction fragment characteristic of the restorer gene indicates that the seedling has the restorer gene. Very large numbers of plants at the seedling stage are screened at much lower cost that the cost of raising the same plants to maturity in the field. In addition, the male fertile phenotype is affected by many different conditions and screening for the presence of the gene by screening for a perfectly linked polymorphism more reliably detect the presence of the gene during this introgression procedure.

EXAMPLE II

Production of New Restorer Cell Lines Through the Introduction of the Restorer Gene Form of GAPC Via Transformation The three plant genotypes of Example I will be considered in accordance with this procedure.

In this example, the problem is precisely the same as that of Example I, namely the transfer of the restorer gene from line R into line B without otherwise altering the characteristics of line B. In this case, however, we will assume that the form of the GAPC gene that represents the restorer gene has been isolated and is available as a cloned DNA segment in a suitable plant *Agrobacterium tumefaciens* transformation vector such as pRD400 (Datla RSS, Hammerlindl J K, Panchuk B, Pelcher L E & Keller W. (1992) Gene 211:383–384). Instead of the lengthy backcrossing program described in Example I, the GAPC gene is transferred to line B through Agrobacterium-mediated transformation.

For the sake of this example, we will also assume that lines A, B and R are *Brassica napus* lines, and that the cloned restorer gene is identical to that of line R. Using the procedure described by Moloney et al. (Moloney, M., Walker, J. & Sharma, K. (1989) Plant Cell Rep. 8:238–242) an Agrobacterium strain harboring the gene in the prRD400 vector is used to inoculate cotyledons from strain B seedlings. The Agrobacterium is eliminated by antibiotic treatment and the resulting plant tissue is placed on media containing the antibiotic kanamycin. pRD400 contains a gene that confers resistance to kanamycin, and hence cells that grow on this antibiotic are likely have acquired the kanamycin gene, along with the restorer gene which is cloned into pRD400. The presence of the restorer gene in these plants is then assessed directly by testing the plants form the presence of restriction fragments characteristic of the restorer using a GAPC probe. It is expected that these plants will be made fertile if they contain the male sterile cytoplasm and that F1 progeny from a cross between line A (as female) and the new transgenic line will also be male fertile.

This method has two distinct advantages: it is much faster and cheaper than conventional plant breeding approaches, requiring only a few months as opposed to years to develop this line. In addition, the presence of the restorer gene will be the only difference between the genome of line B and that of the new restorer line. Thus the integrity of the characteristics of line B are less likely to be compromised.

Although the above description relates to a specific plant species, *Brassica napus,* the invention could be applied to other species provided that the restorer gene in the species corresponds to a specific form of GAPC. In such cases the technique for transformation may differ from that described above.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for detecting the presence of a restorer gene in nuclear genomic DNA of a Brassica plant, said method comprising the steps of:
   i) hybridizing said nuclear genomic DNA under stringent conditions with a probe specific for nuclear restoration of cytoplasmic male sterility of plants, said probe comprising the nucleic acid sequence of SEQ ID NO: 1 or a sufficient hybridizing fragment thereof; and
   ii) detecting hybridization of said probe with said nuclear genomic DNA, wherein said hybridization is indicative of the presence of a restorer gene sequence in said nuclear genomic DNA.

2. A method for detecting the presence of a restorer gene in nuclear genomic DNA of a Brassica plant, said method comprising the steps of:
   i.) amplifying said nuclear genomic DNA under suitable conditions with a primer DNA sequence comprising the nucleic acid sequence of SEQ ID NO: 1 or a sufficient fragment thereof; and
   ii.) detecting amplification of said nuclear genomic DNA, wherein said amplification is indicative of presence of a restorer gene sequence in said nuclear genomic DNA.

* * * * *